United States Patent [19]

Bandlish et al.

[11] Patent Number: 5,266,173

[45] Date of Patent: Nov. 30, 1993

[54] PROCESS FOR PREPARING AROMATIC AMINE COMPOUNDS AND REDUCING AGENT THEREFOR

[75] Inventors: Baldev K. Bandlish; Robert V. Casciani, both of Charlotte, N.C.

[73] Assignee: Sandoz, Ltd., Basel, Switzerland

[21] Appl. No.: 706,144

[22] Filed: May 28, 1991

Related U.S. Application Data

[63] Continuation-in-part of Ser. No. 504,492, Apr. 4, 1990, abandoned.

[51] Int. Cl.$^5$ .............................................. C25B 3/04
[52] U.S. Cl. ................................. 204/72; 204/59 R
[58] Field of Search ............................ 204/59 R, 72

[56] References Cited

U.S. PATENT DOCUMENTS

| | | | |
|---|---|---|---|
| 4,173,521 | 11/1979 | Wade | 204/157.1 R |
| 4,422,917 | 12/1983 | Hayfield | 204/196 |
| 4,971,666 | 11/1990 | Weinberg et al. | 204/59 R |

OTHER PUBLICATIONS

Noel et al, "A Two-Stage Electrosynthesis of 4,4'-Diamino-Stilbene-2,2'-Disulphonic Acid", Indian Journal of Technology, vol. 19, Mar. 1981, pp. 100-101.
Noel et al, "An Electrochemical Technique for the Reduction of Aromatic Nitro Compounds," 12 (1982), 291-298.
Miyanaga et al., "Structures of Hydrated Titanium and Vanadium Ions in Aqueous Solutions Studied by X-Ray Absorption Spectroscopy", Bull. Chem. Soc. Jpn., 63, 3282-3287 (1990).
Hayfield et al., "The Electrochemical Characteristics and Uses of Magneli Phase Titanium Oxide Ceramic Electrodes," presented at Electrochemical Society meeting, May 7-12, 1989.
Comba et al., Inorg. Chem., 1987, 26, 1315-1323.
Cotton et al., *Advanced Inorganic Chemistry*, Fifth Ed., John Wiley & Sons, pp. 654-665 (1988).
Chaussard et al., J. Applied Electrochemistry 16, 803-811 (1986) (with translation).
Gratzel et al., "Raman Spectroscopic Evidence for the Existence of $TiO^{2+}$ in Acidic Aqueous Solutions", Inorg. Chem., 1985, 24, 2320-2321.
Noel, et al., J. Applied Electrochemistry 12 (1982) 291-298.
Abstract, EP 64,629 (1982).
Narasimham et al., "Electrolytic Preparation of Titanous Sulphate", Trans. SAEST vol. 15, No. 2 (1980) 147-162.
Jacobson, *Encyclopedia of Chemical Reactions*, ed. by C. Hampel, vol. VII, Reinhold Pub. Corp. (New York) 1958, 414-415, 420-423.
Lundgren, Rec. Trav. Chim. 75, 585-8 (1956).
Inouye, Chemical Abstracts, 1955, 18, 4950.
Newton, et al., "The Kinetics of the Reduction by Titanous Chloride of Nitrobenzene and its Substitution Products", J. Chem. Soc., 3384-3391 (1953).
Thon, Chemical Abstracts, 1950, 6, 1354.
Swaminathan et al., "Preliminary studies on the electrolyutic reduction of nitrobenzene to aniline", J. Appl. Electrochem. 2 (1972) 169-173.
American Chemical Society, Registry Nos. 12334-0-0-9, 13825-74-6 (1990); 64514-49-4, 13693-11-3, 58428-64-1 (1991).
*Kirk-Othmer Encyclopedia of Chemical Technology*, vol. 23, 168-169.
Aldrich Catalog, 1992, p. 1199.
Merck Index, 11th Ed. (1989) pp. 1492-1493.

*Primary Examiner*—John Niebling
*Assistant Examiner*—Kishor Mayekar
*Attorney, Agent, or Firm*—Robert S. Honor; Richard E. Vila; Diane E. Furman

[57] ABSTRACT

An improved process for reducing aromatic nitro compounds to form the corresponding aromatic amine compounds, and intermediates therefore, and a reducing agent therefor, are disclosed. According to the process, a titanium(IV)oxy salt such as titanium(IV) oxysulfate is electrochemically reduced to form a titanium(III)oxy reducing agent, which can be employed to chemically reduce the aromatic nitro compounds, and the resulting re-oxidized titanium salts may be recycled to the electrochemical reduction step of the process. The titanium-(III)oxy salt product is highly soluble in strong acid solutions and exhibits improved oxidation stability.

29 Claims, No Drawings

PROCESS FOR PREPARING AROMATIC AMINE COMPOUNDS AND REDUCING AGENT THEREFOR

This application is a continuation-in-part of application Ser. No. 07/504,492 filed Apr. 4, 1990, and now abandoned.

BACKGROUND OF THE INVENTION

Various processes have been used to prepare aromatic amine compounds from the corresponding aromatic nitro compounds. Such processes include catalytic hydrogenation, which generally employs high purity catalysts at increased temperatures and pressures; and reduction with iron in dilute hydrochloric acid, which requires extensive product purification as well as disposal of the iron hydroxide sludge which is a by-product.

An electrochemical process has also been developed wherein reduction of the nitro compound is carried out in an aqueous strong acid electrolyte in the presence of a catalytic amount of a redox system, such as that provided by salts of $Ti^{+4}$ and the reduced species thereof comprising salts of $Ti^{+3}$, see, e.g., Noel et al., *J. Applied Electrochemistry* 12 (1982) 291-298. However, the process is impracticable where the starting material or product has low solubility in the acid electrolyte and adheres to or complexes at the electrode, causing a decline in current efficiency. A so-called two-stage electrochemical process has therefore been proposed, Noel et al., *Indian J. Tech.* 19 (1981) 100-101, wherein titanous(III) sulfate salts, having been obtained by electrochemical reduction of titanic sulfate, $Ti(SO_4)_2$, are then employed to chemically reduce the starting aromatic nitro compound. However, Noel and co-workers indicate that titanic sulfate is unstable in low acid solution, and an acid concentration of at least about 10% (wt./vol.) must therefore be maintained to prevent hydrolysis of the titanic sulfate and precipitation of the resulting hydrolyzed titanium compounds. It was further indicated that titanous(III) sulfate obtained by reduction of titanic sulfate has low solubility in aqueous solution and precipitates at concentrations exceeding about 0.5 N. Accumulated undissolved solids at the electrodes can significantly reduce current efficiency.

SUMMARY OF THE INVENTION

The present invention provides new and improved titanium(III) reducing agents, particularly useful, for example, in aqueous media for reducing aromatic nitro compounds to the corresponding aromatic amine compounds and intermediates therefor, and a process for preparing such reducing agents. A two step process is provided by the invention which comprises in step (a) electrochemically reducing a titanium(IV)oxy salt, preferably titanium(IV) oxysulfate ($TiOSO_4$), in an acidic aqueous electrolyte to form a dissolved titanium(III) salt (herein also referred to, inter alia, as a titanium(III)oxy salt); and in a second step (b), employing the thus-obtained titanium(III) salt product as a reducing agent to chemically reduce an aromatic nitro compound to the amine compound.

The titanium(IV)oxy salt to be used in the invention is a water soluble salt generally expressible by the chemical formula TiO(R) wherein R represents one to two anions as required to satisfy the $+2$ valence of the titanium in the remaining titanium oxy ($TiO^{++}$) cationic portion. Such salts are stable, i.e. resistant to hydrolysis in solutions of low, i.e. below about 10% (wt./vol.), strong acid concentration solutions of the titanium(IV)oxy salt. A reduced acid concentration electrolyte is desirable under certain circumstances to provide increased solubility of the titanium(III)oxy salt product, as well as to reduce acid corrosion of the electrodes. Low acid concentration solutions may also be desirable in the subsequent chemical reduction step of the process for stability of certain functionally substituted nitro compounds.

The titanium(III)oxy salt from step (a) advantageously has very good solubility in strong acid aqueous solution, i.e. is soluble at high concentrations, i.e. above 0.5 Normal (equivalent to 0.5 Molar of titanium), of the titanous salt, and more particularly is soluble at concentrations of 1.0 Normal (1.0 Molar) and even higher. Such high concentration aqueous titanium(III)oxy salt solutions may therefore be prepared without resulting in a titanous salt precipitate which can significantly affect current efficiency. For example, an aqueous titanium(III)oxy sulfate solution may be prepared according to the invention, wherein the concentration of the dissolved titanium(III)oxy salt product may be as high as about 3 Normal (Molar equivalents of titanium ion), and is preferably about 0.8 to 2.5. Normal (Molar) and most preferably 1 to 2 Normal (Molar). Also, the titanium(III)oxy salt products have enhanced stability against air oxidation.

Moreover, the titanium(IV) reoxidation product formed from the titanium(III) reducing agent in the course of reduction of the nitro compound in step (b) may be recovered and recycled to step (a) for use as the starting material in an electrochemical reduction to prepare the titanium(III) reducing agent; and this recycling may be continuously repeated without foregoing the advantages provided by the initial titanium(IV)oxy sulfate.

To the best of our knowledge the stable, highly soluble titanium(III)oxy salts as provided by the invention and strong acid aqueous solutions thereof, are novel. Such product is soluble to a high degree and stable, e.g., resistant to hydrolysis and oxidation, in highly acidic solutions and over a wide range of acid concentrations, e.g., acid concentrations of 1–50% (wt./vol.), and preferably 10–50%. Solutions of the titanium(III)oxy product of the invention have the purple color which is characteristic of the dissolved titanium(III) salts. Dissolved titanium(III)oxy salts may be isolated and recovered from such solutions by conventional separation techniques, and the recovered solids may be redissolved and used in reduction step (b) of the invention or for other purposes.

It will be apparent that the invention provides a significant improvement in chemical processes employing reduced titanium salts, particularly in chemical reduction processes such as the reduction of aromatic nitro compounds.

It will also be apparent that certain advantages are provided by the electrochemical reduction process of the invention in the form of reductions in fluid volumes, and equipment and energy savings.

The process of the invention may be employed for the preparation of aromatic amine compounds in general, including unsaturated aromatic amines. The process may also be used to prepare certain intermediates in the formation of aromatic amine compounds from aromatic nitro compounds, such as e.g., aromatic nitroso and aromatic hydroxylamine compounds.

The process is particularly useful to prepare aromatic amine compounds which are fairly insoluble in aqueous solution, or which contain acid-sensitive groups. In particular, the process may be used to reduce 4,4′-dinitrostilbene-2,2′disulfonic acid to 4,4′-diaminostilbene-2,2′disulphonic acid ("DAS"), an important intermediate in the synthesis of optical brighteners which is fairly insoluble in acidic aqueous solutions.

DETAILED DESCRIPTION OF THE INVENTION

The first step of the process of the invention comprises an electrochemical reduction of the titanium(IV)oxy salt in an acidic aqueous electrolyte to form an acidic aqueous solution of the titanium(III)salt reducing agent.

The use of certain titanium(IV)oxy salts in accord with this invention provides for the production of very desirable titanium(III) reducing agents of improved solubility and stability in acidic solutions as well as an improved process for obtaining titanium(III) reducing agents. As indicated, the titanium(IV)oxy salts employed will conform to the basic formula TiOR wherein R represents one or two anions as required to satisfy the +2 valence in the remaining indicated TiO++ cationic portion and provide a titanium(IV)oxy salt which is stable against hydrolysis in highly acidic solution (at a pH value not higher than 1.5., e.g., a pH of about 1.0) over a wide range of acid concentrations. Such titanium(IV)oxy salts may be characterized in particular by stability against hydrolysis at concentrations of strong acids of less than 10% on a weight/volume basis, for example, at a strong acid concentration of 7% (or less), and even as low as about 1%, on a weight/volume basis (total acid to water) at room temperature over a 24 hour period. The stability and hydrolysis resistance of the titanium(IV)oxy salt in solution will be evidenced by the solution remaining clear over time, i.e. substantially free of cloudiness or turbidity or precipitate formation. Such stable titanium(IV) salts upon reduction produce the stable titanium(III)oxy reducing agents having desired high solubility as previously indicated. The titanium(IV)oxy salts employed are also characterized by resulting in titanium(III)oxy reducing agents which are soluble at 1.0 Normal (Molar equivalents of titanium ion) concentrations (or higher) of the titanium(III)oxy product at room temperature in strong acid aqueous solution having a total acid concentration of 20% wt./vol. The titanium(IV)oxy salts, while conforming to the formula TiOR as discussed above, may be prepared and used in the form of complexes with molecules or ligands of water, and possibly various acids, particularly strong acids such as sulfuric acid. The titanium(III)oxy reducing agents prepared from such complexed titanium(IV)oxy salts may themselves be complexed with molecules or ligands of water and possibly various acids, and may be recovered in such complexed form. In general, a variety of substances may be complexed with the titaniumoxy compounds, provided they do not adversely affect the ability of the titanium(IV)oxy salt to remain stable in dilute strong acid solution, e.g., at 7% wt./vol. acid concentration, and do not adversely affect the characteristic improved solubility of the titanium(III)oxy salt.

The significance of R in the formula TiO(R) will be, as indicated, one to two anions which provide a salt stable against hydrolysis as well as the characteristically improved titanium(III)oxy reducing agents. R is preferably inert to the electrochemical reaction conditions and preferably does not significantly affect solubility of the titaniumoxy compound in solution. Various significances of R include sulfate and organic sulfonates, particularly the $C_{1-4}$alkylsulfonates such as methanesulfonate. Mixtures of such compounds or compounds in which R may be different may be formed and used in the solutions employed in carrying out the process of the invention. A particularly preferred titanium(IV)oxy salt is titanium(IV) oxysulfate and in certain embodiments it is advantageously used as starting material and combined in the solution with an organic sulfonic acid.

While the preferred titanium(IV) oxysulfate conforming to its simple formula, $TiOSO_4$ (which alternatively has commonly been expressed as "titanium, oxo[sulfato(2-)-0,0']-," "titanium oxide sulfate" or "titanyl sulfate"), may be employed, other forms thereof which include water of hydration as well as complexed strong acid molecules have been found suitable for use. For example, the compound described as "titanium, oxo[sulfato(2-)-0,0'], complexed with sulfuric acid, hydrate" (CAS Registry No. 123334-00-9), for which is given the molecular formula $H_2O_4S.H_2O.O_5STi$, may satisfactorily be used. This compound is commercially available from Aldrich Co. or Noah Chemical Corp., San Antonio, Tex. (under the molecular formula $TiOSO_4.xH_2O.yH_2SO_4$) in a granulated solid form. The term "titanium(IV) oxysulfate" as used herein shall be understood to include the compound in its hydrated and/or acid complexed forms. When dissolved in water, the commercial compound forms a dilute sulfuric acid solution of the titanium(IV) oxysulfate. The titanium(IV)oxy salt is in general desirably free of metals, metallic compounds and other contaminants which would substantially interfere with the electrochemical reduction process or the solubility properties of the titanium compounds.

Preferably, the concentration of the titanium(IV)oxy salt in the aqueous solution thereof is selected to provide, following reduction under the given reducing conditions, a concentration of the resulting titanium(III)oxy salt in the said aqueous solution, of about 0.1 to about 3M, more preferably about 0.8 to 2.5Molar, and most preferably about 1.0 to about 2.2M.

The electrochemical reduction may be performed using a standard electrolytic cell, including divided cells and undivided cells.

In a divided electrolytic cell, i.e. having a compartment containing a cathode wherein reduction occurs, and a compartment containing an anode wherein oxidation occurs, the two compartments are generally divided by a porous barrier which regulates the mobility of ions, e.g., by permeating $H^+$ ions which migrate from the anodic compartment to the cathodic compartment while preventing migration of titanium ions to the anode. The barrier may comprise a ceramic porous diaphragm, ion exchange membrane (e.g., a Nafion$^T$ membrane) or other type of membrane. In such divided cells, the cathode may be made from any conventional suitable metal, such as copper or lead, and is preferably of copper. The anode preferably comprises platinum, platinum coated over an inert support such as niobium or titanium, or other suitable material.

Suitable electrolytic cells which can be employed with a porous barrier as divided cells are an H-type cell, which is usually employed in small scale operations, and a plate and frame cell.

In the process of the invention, an aqueous electrolyte solution comprising titanium(IV)oxy salt is added to the cathodic compartment, and an aqueous electrolyte is employed in the anodic compartment.

The catholyte preferably comprises a water solution of the titanium(IV)oxy salt. It will be recognized that a low acid concentration solution (e.g., about 1 to 10% (wt./vol.)) is effectively obtained by dissolving commercially available titanium(IV) oxysulfate, as described above, in water.

However, if desired, e.g., to improve conductivity of a low concentration titanium salt solution, acid concentration of the catholyte can be increased by addition of strong acid, to provide a total acid concentration (including any acid component provided by the titanium(IV)oxy salt starting material) of about 1 to 50% (wt./vol.), and preferably about 5 to 20% (wt./vol.). In any case, the pH of the electrolyte and resulting product solution will be at a value not exceeding 1.5 and is preferably about pH 1.0 or lower.

The added acid may comprise sulfuric acid or another suitable inorganic acid, or mixtures thereof. However, it has been discovered, and is an aspect of this invention, that improved solubility and stability of the titanium(III)oxy salt is obtained in the presence of organic sulfonic acids which may comprise substantially all or a part of the strong acid component of the aqueous titanium(oxy) solutions. Hence, in one embodiment, such improvements are obtained in aqueous sulfuric acid solutions whose acid concentration is increased if the added acid component thereof (i.e., in excess of any acid component provided by the titanium oxysulfate starting material) comprises an organic sulfonic acid. In terms of stability, not only is the reducing agent resistant to hydrolysis but it has also been found that such titanium(III)oxy product is substantially improved at all acid concentrations with regard to oxidation resistance, such that the process and product may be utilized without the need for maintaining an inert atmosphere to protect against such oxidation. Such enhanced resistance to oxidation is also exhibited even if the titanium(III)oxy salt is recovered as a solid from sulfuric acid solutions in which it is prepared.

Such organic sulfonic acids include aromatic acids such as the substituted and unsubstituted phenylsulfonic acids, e.g., p-toluene-sulfonic acid, and preferably, the lower alkyl acids, i.e. $C_{1-4}$ alkylsulfonic acids, such as methanesulfonic acid, propanesulfonic acid, and butanesulfonic acid, of which methanesulfonic acid ($CH_3SO_3H$) is most preferred.

It will be recognized that the reduction of titanium(IV) oxysulfate to titanium(III)oxy reducing agent, for example, will itself result in increased acid strength of the solution, which should be taken into account in considering total acid strength.

The anolyte generally comprises an aqueous (1–50% (wt./vol.)) acid solution. The pH of the anolyte solution should be maintained below about 6 and preferably below about 5. Strong acids, e.g., sulfuric acid, or an inert salt which will increase conductance may be included in the anolyte. Optionally, the anolyte may also comprise an amount of a suitable redox agent which will be oxidized at the anode as titanium(IV) is reduced at the cathode. Examples of suitable redox agents are salts of transition metals, such as cerium III, cerium IV (e.g., ceric methanesulfonate, cerous nitrate), manganese II (e.g., manganous sulfate), chromium II, chromium III, etc., which can be oxidized to a higher transition state; as well as hydrogen halides, such as hydrochloric acid and hydrobromic acid, which are oxidized to form halogens. However, the anolyte should not comprise mono- or divalent ions which would tend to permeate the porous barrier and be reduced at the cathode to form a basic solution (e.g., $Na+$, $K+$).

It has been found, and is an aspect of this invention, that under certain conditions an undivided electrolytic cell may also be employed for electrochemical reduction of titanium(IV)oxy salt, which advantageously eliminates certain costs and technical difficulties associated with maintaining the porous barrier of a two-compartment cell.

In such undivided cells, wherein an electrode system comprising both cathodically and anodically active sites is immersed in a common aqueous strong acid electrolyte solution, reduction of titanium(IV)oxy salt occurs at the cathode and a corresponding oxidation reaction occurs at the anode. The cathode may be formed of conventional materials, e.g., copper or lead. It is critical, however, that the anode be formed of material which does not participate generally or under the given conditions, in reactions which prevent net formation of the titanium(III)oxy product. For example, it is important when employing an undivided electrolytic cell in the present process that the titanium(III) product not be re-oxidized at the anode to the extent that the titanium(IV) starting material is significantly regenerated.

Certain ceramic-like oxides of titanium have been found useful to comprise the anode in an undivided electrolytic cell in the process of the present invention.

Such materials, which are obtained by high temperature reduction of $TiO_2$, are represented in general by the formula $TiO_{[x]}$ where x is a number from 1.55 to 1.95, preferably 1.65 to 1.9, more preferably 1.65 to 1.85, and most preferably 1.7 to 1.8. Certain of the oxides which correspond to a structure wherein x is within the foregoing ranges, expecially $Ti_4O_7$ and $Ti_5O_9$, are available in the form of EBONEX$^T$ electrodes from Ebonex Technologies, Inc., the assignee of U.S. Pat. No. 4,422,917, which is hereby incorporated by reference in its entirety.

The aqueous strong acid electrolyte solution which is employed in the undivided cell generally has a total acid concentration of 1 to 50% (wt./vol.) strong acid, and preferably about 5 to 25% (wt./vol.), and most preferably about 10 to 20% (wt./vol.). Total acid concentration will be understood to include any acid component provided by the starting titanium(IV) oxysulfate material.

It has been found that higher current efficiencies are obtained if the strong acid comprises a sulfonic acid such as a $C_{1-4}$ alkyl sulfonic acid, particularly methanesulfonic acid. Therefore, it is preferred when performing the process in an undivided electrolytic cell, that the aqueous strong acid electrolyte solution comprises an organic sulfonic acid such as a $C_{1-4}$ alkyl sulfonic acid, preferably methanesulfonic acid, preferably in a concentration of about 5% to 25% (wt./vol.).

In general, in systems employing an organic sulfonic acid for its greater benefits, it may be preferred that said organic sulfonic acid solutions not comprise in excess of about 10% (wt./vol.) of other acids such as sulfuric acid (inclusive, for example, of any sulfuric acid component provided by the preferred titanium(IV) oxysulfate starting material). In such systems and others, a concentration of from 3% to 25% wt./vol., preferably 10% to 20%, of the organic sulfonic acid may be added primarily to enhance the oxidation resistance of the titanium(III) product to a level desired for the particular operation.

The current conditions and reaction temperatures employed in the process using a divided or undivided electrolytic cell are generally the same. To carry out the electrochemical reduction, a direct current is applied to the electrodes under conditions sufficient to result in the reduction of titanium(IV)oxy salt to titanium(III) product. Generally, a current density of about 1–30 amperes per square decimeter (ASD) is employed, preferably about 5–20 ASD. Current ranges of about 1–8 ASD, including about 2.5 to 3.5 ASD, can also give useful results. Current efficiency is generally expressed as: the coulombs of electricity which are actually employed for reduction of titanium(IV)oxy salt to the titanium(III)oxy product, as a percent of the theoretical number of coulombs of electricity required therefor. Advantageously in the process of the invention, a high current efficiency which remains fairly constant over the reaction time may be achieved.

Current is applied for a time sufficient to result in the reduction of at least a portion of the titanium(IV)oxy salt to the titanium(III)oxy product.

In the course of the reduction reaction, the catholyte will comprise mixtures of titanium salts in both the Ti(IV) and Ti(III) state.

The temperature of the electrolyte solutions should be maintained at elevated temperature, e.g., about 25°–65° C., and preferably about 45°–50° C. The electrolyte solution wherein titanium(III)oxy product is formed is preferably agitated during heating by a stirring bar and magnetic stirrer or by other means.

Air oxidation of the resulting titanium(III)oxy product may be prevented using, for example, an inert gas, such as nitrogen, by bubbling the gas through the reaction solution and/or as an inert atmosphere, as the particular type of cell or operation requires. However, even the titanium(III)oxy salts prepared in strong acid solutions in the absence of organic sulfonic acids exhibit enhanced oxidation resistance compared to other titanium(III) reducing agents. Hence, an inert condition may or may not be desired depending on the desired shelf-life of the product. In general, strong acid solutions of the titanium(III)oxy salts show resistance to oxidation to the extent of at least 60% after bubbling air through such solutions for one hour at room temperature (total acid concentration 20% wt./vol.) and many such solutions, particularly those with an organic sulfonic acid, show little or no oxidation after such a strenuous test (e.g., 98% or better resistance to oxidation).

As reduction of the titanium(IV)oxy salt progresses, the electrolyte solution, initially clear, takes on the deep purple color of the reduced titanium salts being formed therein.

The progress of the electrochemical reduction may be quantitatively monitored by conventional means, such as by titration with ferric, Fe(III), ions, see, e.g., Vogel, *A Textbook of Quantitative Inorganic Analysis—Including Elementary Instrumental Analysis* (3rd Ed.), 1961, John Wiley & Sons, Inc., p. 330.

The resulting titanium(III)oxy product which has formed in the electrolyte may be employed as a reducing agent in chemical reductions, such as those in which other titanous reducing agents have been employed, and in particular to chemically reduce aromatic nitro compounds. The advantages of the invention may lead to expanded usage in reduction reactions.

The process of the invention is particularly suitable for the reduction of aromatic nitro compounds which form a fairly insoluble amine product, such as 4,4'-diaminostilbene-2,2'-disulfonic acid. Following electrochemical reduction, the aromatic nitro compound is combined with the titanium(III)oxy reducing agent in a reaction medium under conditions suitable for formation of the corresponding aromatic amino compound.

Aromatic nitro compounds which form a soluble reduced product may be present in the electrolyte solution during the electrochemical reduction step (a) of the process, and will be reduced in situ by the titanium(III)oxy product which forms.

The molar ratio of titanium(III) to the aromatic nitro compound is preferably about 6N:1 to 7N:1, wherein N is the number of nitro groups in the nitro compound.

The reaction medium comprises an aqueous strong acid, such as sulfuric acid, but more preferably, comprises an organic sulfonic acid, preferably a $C_{1-4}$alkyl sulfonic acid, especially methanesulfonic acid.

Acid concentration of the reaction medium is suitably about 1 to 50% (wt./vol.), and preferably about 5–25% (wt./vol.).

It is an advantage of the process of the invention that, in one embodiment, a low acid concentration titanium(IV)oxy salt electrolyte solution can be employed for electrochemical reduction; and in the subsequent chemical reduction step, acid concentration can optionally be increased.

In a preferred embodiment of the invention, the reaction medium comprises the purple aqueous titanium(III)oxy salt solution which results from the prior electrochemical reduction step (a), and which then optionally has been diluted or reconcentrated by addition of water or make-up acid to the desired acid concentration for the chemical reduction.

In an alternative embodiment, the titanium(III)oxy salts are recovered and redissolved in an appropriate medium before combining with the starting nitro compounds of the invention. Such salts may be recovered from the solutions in which they are formed by the simple removal, e.g., by evaporation, of water from such solutions. Preferably, such salts are recovered from solution having a total acid concentration of 1% to 25% wt./vol., preferably 5% to 20% wt./vol.

To initiate chemical reduction of the aromatic nitro compound, the reaction medium is heated to a temperature, for example, of about 50°–100° C., preferably about 70°–80° C., and it is maintained at such elevated temperature for a time sufficient that at least a portion of, and preferably all or substantially all of, the aromatic nitro compound has been reduced.

Where the starting aromatic nitro compound (e.g., 4,4'-dinitrostilbene-2,2'-disulfonic acid) is fairly insoluble in aqueous solution, a slurry is formed by introducing the nitro compound into the reaction medium, and reaction occurs interfacially between the insoluble nitro compound and the dissolved titanium(III) reducing agent, to form the corresponding amine product, which in the case of 4,4'-diaminostilbene-2,2'-disulfonic acid, is deposited as a white solid.

As the reduction of the aromatic nitro compound proceeds, it is accompanied by re-oxidation of at least a part of the purple-colored titanium(III)oxy salt solution to the colorless titanium(IV)oxy salt solution. Therefore the progress of the reaction is typically evidenced by a change in color of the reaction medium from purple to clear-to-light yellow. As in the electrochemical reduction step, the reduction of the nitro compound can be quantitatively monitored by known techniques, e.g., titration of a sample with Fe(III).

A purple color of the reaction medium following substantially complete reduction of the starting aromatic nitro compound indicates the presence in solution of an excess of titanium(III)oxy salt.

Once reduction of the aromatic nitro compound is determined to be substantially complete, the resulting aromatic amine product may be recovered.

Any unreacted nitro compound may be recovered from the solution, generally by filtration.

Where the amine compound is insoluble in aqueous acid solution, it may be recovered by simple filtration, and then optionally purified by conventional techniques, such as by dissolving in a strong base such as sodium carbonate, filtering out the insoluble materials, combining with an aqueous acid solution and reprecipitating therefrom.

A soluble amine product may be collected by various techniques which generally involve precipitating and filtering the compound from solution.

The remaining solution comprises the reoxidation products of the titanium(III)oxy salt, and any excess titanium(III)oxy salt. This solution, having optionally been diluted or reconcentrated to a desired acid concentration, may be recycled to an electrochemical reduction step (a) according to the present process in order to again obtain a solution of titanous salts, for use as a reducing agent of an aromatic nitro compound, in a second and further repeated chemical reduction steps.

Thus an advantage of the overall process of the invention is that it may be carried out efficiently on a continuous or semi-continuous basis with little or substantially no loss of the advantages realized in the process as initially conducted.

While the chemical formula for various titanium compounds is known, including the formula of the titanium(IV) oxysulfate exemplified herein, the chemical formula of the titanium(III)oxy salts produced herein has not been totally ascertained. Also, the molecular structure of the titanium(IV)oxy compounds is uncertain and hence we cannot be bound by any particular theory concerning the mechanisms involved or any particular structures from which advantages may arise, particularly with regard to the titanium(III)oxy reducing agents. However, given the observations made in our work, the unusually good stability of the products in strong acid solution (and as recovered therefrom) indicates the presence of cations or cationic moieties in which oxygen is stably bound to titanium to provide a fundamental titaniumoxy formula when titanium is in both the plus four and plus three valence states. The stability is such as to be consistent in both valence states with the stable polymerized titaniumoxy structure postulated for titanium(IV)oxy structures by Cotton, et al. *Advanced Inorganic Chemistry*, Fifth Ed., Wiley Interscience, pp 654-656 (1988). See also Lundgren, G., *Rec. trav. chim.* 75, 585-8 (1956). Thus in the formula Ti-O(R), R can be postulated to comprise a polymer or oligomer having Ti—O—Ti bridges, wherein each Ti may be associated with one or more of various ligands. Such consistency is indicated by the fact that the titanium(III)oxy reducing agent when oxidized in the reducing step (b) produces a titanium(IV)oxy salt which is indistinguishable in terms of its basic advantages when recycled to step (a) even if the recycled product is different than the starting titanium(IV)oxy salt. For example, if the process is started with titanium(IV) oxysulfate complexed with sulfuric acid and no different acid is introduced in the process, the reoxidized titanium(IV)oxy salt recycled to step (a) and its performance are indicated to be essentially indistinguishable from the process as initially conducted. On the other hand, if an organic sulfonic acid is added when starting with, e.g., the indicated commercially available titanium(IV) oxysulfate complexed with sulfuric acid, the reoxidized titanium(IV)oxy product recycled to step (a) is indicated to involve mixed salts or mixtures of salts which offer not only the basic advantages of starting titanium(IV) oxysulfate but also the additional advantages of the organic sulfonic acid. Hence, such mixed salts and mixtures of salts are encompassed by the invention. Titanium(IV)oxy compounds involving organic sulfonate salt forms (conforming, e.g. to a $TiO(OSO_2CH_3)_2$ formula) may be formed and used to similar advantage as starting materials in the process. For example, in our experiments, we neutralize the commercially available titanium(IV) oxysulfate in aqueous solution with triethylamine (to pH 5.5) to obtain a white solid which was redissolved in methanesulfonic acid to provide a titanium(IV)oxy salt solution which performed consistent with the invention.

All acid concentrations herein are expressed as percentages based on weight of acid by volume of solution, and reflect molecules of acids actually added or present or available in materials added, such as available in the indicated commercially available titanium(IV) oxysulfate, and hence does not reflect or include potential acids or acidic conditions such as those formable or induced by the sulfate anions in an oxysulfate when hydrolyzed in water.

The following examples are intended to be illustrative only and not limitative of the invention.

In the examples, unless otherwise indicated, the titanium(IV) oxysulfate, $TiOSO_4 \cdot xH_2O \cdot yH_2SO_4$, in powder form, is obtained from Aldrich Chemical Company. In Examples 1-9 the titanium(IV) compound comprises by weight 19.1% titanium, 15.2% sulfuric acid, and 8% water. 4,4'-dinitrostilbene-2,2'-disulfonic acid is obtained from Pfaltz and Bauer Corp. Methanesulfonic acid, $CH_3SO_3H$, (70%) is obtained Pennwalt Corp.

EXAMPLE 1

(a) An H-type cell (The Electrosynthesis Co.) equipped with a potentiostatic controller, DC power supply, coulometer, a 100A shunt, and Haake circulator, is employed for the electrochemical reduction.

An R-1010 ion exchange membrane (The Electrosynthesis Co.) separates the anodic and cathodic compartments. The cathode is copper and the anode is platinum (each 25 cm. sq.). A side tube connected to the cathodic compartment serves as a reference compartment, in which a saturated calomel electrode is inserted.

200 ml. of a clear 1 Molar water solution of titanium(IV) oxysulfate is added to the cathodic compartment. The resulting solution is calculated to have a sulfuric acid concentration of 3.8%. Nitrogen is bubbled through the solution.

70 ml. of aqueous 25% sulfuric acid is added to the anodic compartment. The reference compartment also contains aqueous 25% sulfuric acid.

The temperature of the solutions is maintained at 44°-54° C.

A direct current is then applied to the electrodes by maintaining the working potential at about 0.34 V to 0.44 V with reference to the saturated calomel electrode. Current density is maintained below 2.4 ASD.

After passing 9,398 coulombs over about 9.8 hours, the current is removed, and current efficiency is determined to be 88% after 48.7% of the theoretic current is passed.

The resulting dark purple solution in the cathodic compartment is recovered. No precipitate is observed. Titration of a sample with ferric ammonium sulfate indicates that 0.085 mole of titanium(III) oxysulfate is present in solution.

(b) To the recovered dark purple solution of titanium(III) oxysulfate is added 2.7 g. (6.2 mmoles) of 4,4'-dinitrostilbene-2,2'-disulfonic acid. The resulting slurry is heated to a temperature of about 75° C., with stirring, and is maintained at 75° C. for 30 minutes. The solution is then allowed to cool to room temperature (about 25° C.).

The deposited white solid is collected by filtration, washed with water, and dried at reduced pressure (20 mm Hg), to give 1.83 g. (4.9 mmole) of 4,4'-diaminostilbene-2,2'-disulfonic acid.

(c) The purple filtrate is then re-subjected to the electrochemical reduction procedure of part (a) above, and the resulting 92 ml. of 1.23M solution of titanous salt is employed to treat a second batch of 4,4'-dinitrostilbene-2,2'-disulfonic acid, according to the procedure of part (b).

EXAMPLE 2

(a) A multipurpose plate and frame cell (Electro MP-Cell from Electrocell AB) equipped with a DC power supply, coulometer (The Electrosynthesis Co.), 100A shunt, glass reservoirs, PVDF rotameters, pumps, and a Haake circulator, is employed for electrochemical reduction.

A Nafion 324 ion exchange membrane separates the anodic and cathodic compartments. The cathode is copper (100 sq. cm.) and the anode is platinum coated over titanium (100 sq. cm.). The electrodes are separated by a distance of 1.5 cm.

A nitrogen atmosphere is maintained in the cathodic compartment.

1100 ml. of a clear aqueous solution is prepared by combining 250 g. titanium(IV) oxysulfate and 180 g. of concentrated sulfuric acid in water. The resulting solution has a sulfuric acid concentration of 19.8%, and a titanium(IV) oxysulfate concentration of 0.91 Molar.

2100 ml. of an aqueous solution comprising 360 g. of sulfuric acid is prepared. The solution, which has an acid concentration of 17.1% is added to the anodic compartment.

The temperature of the solutions is maintained at about 45° C.

A direct current of 3 amperes is applied to the electrodes over about 8.2 hours, current density being maintained at about 3 ASD. The current efficiency is 80.7% after 92.9% of the theoretical current is passed.

The dark purple solution which is then recovered from the cathodic compartment has a volume of 1250 ml. Titration of a sample with ferric ammonium sulfate shows that the concentration of titanium(III) oxysulfate in the solution is 0.6M. No precipitate is observed.

(b) To 1.125 liters of the recovered dark purple solution of titanium(III) oxysulfate is added 23.5 g. (about 54 mmoles) of 4,4'-dinitrostilbene-2,2'-disulfonic acid. The resulting slurry is heated to a temperature of about 78° C., with stirring, at which temperature it is maintained for one hour, as a white solid. The solution is allowed to cool to room temperature. Titration of a sample with ferric ammonium sulfate indicates that 0.573 moles of titanium(III)oxysulfate have been consumed.

The deposited white solid is collected by filtration, washed with water, and dried at reduced pressure, to give 17.4 g. (about 46 mmoles) of 4,4'-diaminostilbene-2,2'-disulfonic acid.

EXAMPLE 3

(a) The Electro MP-Cell apparatus of Example 2, part (a) is employed, with the exception that there are two cathodes and two anodes.

900 ml. of a clear aqueous solution containing 300 g. of titanium(IV) oxysulfate and 285.6 ml. of 70% methanesulfonic acid is prepared. The resulting solution has a total acid concentration of about 35% (comprising about 5% sulfuric acid and 30% methanesulfonic acid) and a titanium(IV)oxy salt concentration of 1.33 Molar.

1100 ml. of a solution comprising 300 ml. of 70% methanesulonic acid (i.e. having an acid concentration of 25.7% is added to the anodic compartment.

The temperature of the solutions is maintained at about 45° C.

102,000 coulombs are passed by applying a direct current to the electrodes for about 6.3 hours (current density being maintained at 3.0-2.12 ASD), and current efficiency is 90.7%.

The resulting dark purple solution which is recovered from the cathodic compartment has a volume of 1050 ml. Titration of a sample with ferric ammonium sulfate shows that the concentration of titanium(III)oxy salt in the solution is 0.913M. No precipitate is observed.

(b) To 580 ml. of the recovered dark purple solution of titanium(III)oxy salt is added under nitrogen, 21.5 g. (about 0.05 mole) of 4,4'-dinitrostilbene-2,2'-disulfonic acid. The resulting slurry is heated to a temperature of about 82° C., with stirring, at which temperature it is maintained for one hour, as a white solid appears. The solution is allowed to cool to room temperature. Titration of a sample with ferric ammonium sulfate indicates that 0.479 moles of titanium(III)oxy salt have been consumed.

The deposited white solid is collected by filtration, washed with water, and dried at reduced pressure, give 14.0 g. (about 0.037 moles) of 4,4'-diaminostilbene-2,2'-disulfonic acid.

EXAMPLE 4

(a) The Electro MP-Cell apparatus of Example 3 is employed.

840 ml. of a clear water solution comprising 490.7 g. of titanium(IV) oxysulfate is prepared. The resulting 2.24M titanium(IV) oxysulfate solution having an acid concentration of about 8.5% is added to the cathodic compartment.

2,100 ml. of an aqueous 25% sulfuric acid solution are added to the anodic compartment.

The temperature of the solutions is maintained at about 45° C.

117,000 coulombs are passed by applying a direct current to the electrodes over about 6.7 hours (current density being maintained at 2 to 2.5 ASD), and current efficiency is determined to be 99% after 50.5% of theoretical current is passed.

The resulting dark purple solution which is recovered from the cathodic compartment has a volume of 1090 ml.

Titration with ferric ammonium sulfate shows that the concentration of titanium(III) oxysulfate in the solution is 1.1M. No precipitate is observed.

(b) To 537 ml. of the recovered dark purple titanium(III) oxysulfate solution is added 21.7 g. (about 0.05 mole) of 4,4'-dinitrostilbene-2,2'-disulfonic acid. The resulting slurry is heated to a temperature of about 80° C., with stirring, at which temperature it is maintained for 1 hour, as a white solid appears. The solution is allowed to cool to room temperature.

The deposited white solid is collected by filtration, washed with water, and dried at reduced pressure, to give 17.5 g. (about 0.046 mole) of 4,4'-diaminostilbene-2,2'-disulfonic acid.

EXAMPLE 5

A 100 ml. beaker equipped with a potentiostatic controller, DC power supply, coulometer, a 100A shunt, magnetic stirrer and heat source, with a copper cathode (20 sq.cm.) and an Ebonex ® anode (20 sq.cm.), is employed as an undivided cell for electrochemical reduction. A saturated calomel electrode is used as a reference electrode. A clear aqueous solution is prepared by combining in the cell 17 g. (0.068 moles) of titanium(IV) oxysulfate and 22.5 g. methanesulfonic acid in water. The resulting electrolyte solution has a total acid concentration of about 36.8% (comprising 3.8% sulfuric acid and 33% methanesulfonic acid). Nitrogen is continuously bubbled through the electrolyte solution.

A current potential of 0.44 with reference to SCE is applied at a temperature of about 45°–60° C., current density being maintained at about 1–1.5 ASD. 4,206 coulombs are passed.

Titration of a sample of the resulting purple colored electrolyte solution with ferric ammonium sulfate indicates that 18.7 mmoles of titanium(III)oxy product are present in solution.

Current efficiency is calculated to be 42.9%.

EXAMPLE 6

The undivided apparatus of Example 5 is used, except that a 300 ml. beaker is employed as the electrolytic cell. 150 ml. of a clear aqueous solution is prepared by dissolving 25 g. (0.1 mole) of titanium(IV) oxysulfate in water. The resulting solution is 0.66 Molar. The resulting electrolyte solution has a total acid concentration of about 2.5%.

2.146 coulombs are passed at a constant potential of 0.44 with respect to SCE at a temperature of 49°–58° C. A purple colored solution is recovered which contains about 2.24 mmoles of titanium(III) oxysulfate.

The current efficiency is 10%.

EXAMPLE 7

A portion of the recovered light purple solution of Example 6, comprising 1.7 mmoles of titanium(III) oxysulfate, is transferred to the cathodic compartment of the divided H cell used in Example 1.

The anolyte comprises 40 ml. of an aqueous 20% sulfuric acid solution.

4,202 coulombs are passsed at a constant potential of 0.52 volts with respect to SCE.

Titration of the resulting dark purple solution with ferric ammonium sulfate shows that 27.5 mmoles of titanium(III)oxy product are present in solution.

Current efficiency is determined to be 59.4%.

EXAMPLE 8

The undivided cell apparatus of Example 6 is used.

150 ml. of a clear aqueous solution is prepared by combining 25 g. (0.1 mole) of titanium(IV) oxysulfate and 30 g. of sulfuric acid in water. The resulting solution has a total acid concentration of 22.5%.

6,061 coulombs are passed at a constant potential of 0.44 with respect to SCE at a temperature of 50°–58° C.

Titration with ferric ammonium sulfate shows that 3.09 mmoles of titanium(III) oxysulfate are present in solution.

Current efficiency is determined to be 5.0%.

EXAMPLE 9

The undivided cell apparatus of Example 6 is used.

150 ml. of a clear aqueous solution is prepared by dissolving 25 g. (0.1 mole) of titanium(IV) oxysulfate and 30 g. of methanesulfonic acid. The resulting solution has a total acid concentration of about 22.5% (comprising about 2.5% sulfuric acid and 20% methanesulfonic acid) and a titanium(IV)oxy salt concentration of 0.015M.

5,900 coulombs are passed at a constant potantial of 0.44 with respect to SCE at a temperature of 42°–56° C.

Titration with ferric ammonium sulfate shows that 31.6 mmoles of titanium(III)oxy product are present in 106.8 ml. of solution, i.e. providing a concentration of titanium(III)oxy salt of approximately 0.3M.

Current efficiency is 51.6%.

EXAMPLE 10

The H-cell apparatus of Example 1 is employed, and nitrogen is bubbled through the catholyte.

100 ml. of a clear water solution comprising 37.5 g. of titanium(IV) oxysulfate (Aldrich Co.) (which is determined to comprise 5.62 g. of sulfuric acid) and 25 g. of methanesulfonic acid is prepared. The resulting 1.5M titanium(IV)oxy salt solution having a total acid concentration of about 30.6% is added to the cathodic compartment and the reference compartment.

40 ml. of an aqueous 25% sulfuric acid solution are added to the anodic compartment.

The temperature of the solutions is maintained at about 50° C.

A current potential of 0.2–0.4 V with reference to SCE is applied. 9,650 coulombs are passed by applying a direct current to the electrodes over about 5 hours.

25 ml. of the resulting dark purple solution which is recovered from the cathodic compartment is titrated with ferric ammonium sulfate and is determined to have a titanium (III)oxy salt concentration of 0.957M.

The remaining solution is futher electrolyzed by passing 1,286 coulombs over a period of 70 minutes. The resulting solution has a titanium(III)oxy salt concentration of 1.43M without precipitate.

Current efficiency is determined to be 98%.

EXAMPLE 11

The H-cell apparatus of Example 1 is employed, with the exception that no inert gas is bubbled through the solutions.

100 ml. of a clear water solution comprising 25 g. of titanium(IV) oxysulfate (Aldrich Co.) (which is determined to comprise 3.75 g. of sulfuric acid) is prepared. The resulting 1.5M titanium(IV) oxysulfate solution having a total acid concentration of about 3.7% is added to the cathodic compartment and the reference compartment.

40 ml. of an aqueous 20% sulfuric acid solution are added to the anodic compartment.

The temperature of the solutions is maintained at about 50° C.

A current potential of 0.45–0.75 V with reference to SCE is applied. 9100 coulombs are passed by applying a direct current to the electrodes over about 6.3 hours.

The resulting dark purple solution which is recovered from the cathodic compartment is evaporated by heating to a temperature of about 95° C. at reduced pressure (20–25mm Hg.) to yield a purple solid, 15.6 g (0.1M).

Current efficiency is 81.5% after 94.3% of theoretical current is passed.

12 g. of the obtained solid is redissolved in 100 ml. of water, and titration of the resulting solution with ferric ammonium sulfate shows that 76.9 mmoles of titanium(III)oxy sulfate are present in solution.

To the above-prepared aqueous titanium(III) oxysulfate solution is added an amount of water to provide a total volume of 128 ml. 101 ml. of this solution containing 45.1 mmoles of the titanium(III) oxy salt is subjected to air bubbling for one hour.

After one hour of air bubbling, titration of a sample of the solution with ferric ammonium sulfate shows that 41.4 mmoles of titanium(III)oxy sulfate salt are present in solution, indicating that 8.2% of the titanium(III)oxy salt has been oxidized.

EXAMPLE 12

The H-cell apparatus of Example 1 is employed, with the exception that no inert gas is bubbled through the solutions.

100 ml. of a clear water solution comprising 25.0 g. of titanium(IV) oxysulfate (which is determined to comprise 19.7% titanium, 20% sulfuric acid, and 6.9% water) is prepared.

To the thus-formed aqueous 1.0M titanium(IV) oxysulfate solution is added an amount of triethylamine to raise the pH to about 5, and the resulting mixture is stirred for two hours and then filtered at reduced pressure and washed with water, to yield a white solid, which is air dried to yield 37 g. of partially dry product.

5 g. of triethylamine are added to the filtrate, but no additional formation of white solid is observed.

20 g. of the partially dried solid is dissolved in 100 ml. of 20% methanesulfonic acid which is added to the cathodic compartment of the electrolytic cell.

2,648 coulombs of electricity are passed at a constant potential of 0.5 V, at a temperature of about 50° C.

Titration of a sample of the resulting purple solution which is withdrawn from the cathodic compartment with ferric ammonium sulfate indicates that 25.7 mmoles of titanium(III)oxy salt are present in solution.

The current efficiency is determined to be 93.7%.

EXAMPLE 13

(a) The H-cell apparatus of Example 1 is employed, with the exception that no inert gas is bubbled through.

100 ml. of a clear water solution comprising 25 g. of titanium(IV) oxysulfate (which is determined to comprise 5.0 g. of sulfuric acid) and 15.0 g. of sulfuric acid is prepared. The resulting 1M titanium(IV) oxysulfate solution having an acid concentration of about 20% is added to the cathodic compartment and the reference compartment.

40 ml. of an aqueous 20% sulfuric acid solution are added to the anodic compartment.

The temperature of the solutions is maintained at about 45°–50° C.

4050 coulombs are passed by applying a direct current to the electrodes over about 1.4 hours. (current density being maintained at 2.5 to 3.4 ASD), and current efficiency is determined to be 96.7%.

Air is bubbled through 94 ml. of the above-prepared solution (containing 38.56 mmoles of titanium(III) oxysulfate) for a period of one hour. Titration of a sample of the resulting solution shows that 37.05 mmoles of the titanousoxy salt are present in solution, indicating that 4.0% of the titanousoxy salt is oxidized during one hour of air bubbling.

In another experiment, air is bubbled for one hour through a titanium(III) oxysulfate solution having a total sulfuric acid concentration of 30% wt./vol. with less than 10% of the titanium being reoxidized to titanium(IV).

EXAMPLE 14

The H-cell apparatus of Example 1 is employed.

125 ml. of a clear water solution comprising 25 g. of titanium(IV) oxysulfate (Aldrich Co.) (which is determined to comprise 5.0 g. of sulfuric acid) and 42 g. of methanesulfonic acid is prepared. The resulting 0.8M titanium(IV)oxy salt solution having a total acid concentration of about 37.6% is added to the cathodic compartment and the reference compartment.

45 ml. of an aqueous 40% sulfuric acid solution are added to the anodic compartment.

The temperature of the solutions is maintained at about 45°–55° C.

6,000 coulombs are passed by applying a direct current to the electrodes over about 1.7 hours (current density being maintained at 2.6 to 4.3 ASD).

The resulting dark purple solution which is recovered from the cathodic compartment has a volume of 116 ml. Titration of a sample with ferric ammonium sulfate shows that 59.8 mmoles of titanium(III)oxy salt are present in solution.

Current efficiency is determined to be 96.1%.

Air is bubbled through 111 ml. of the above-prepared solution (containing 57.02 mmoles of titanium(III)oxy salt) for a period of one hour. Titration of a sample of the resulting solution showed that 56.7 mmoles of titanous salt are present, indicating that 0.87% of the titanous salt is oxidized during one hour of air bubbling.

EXAMPLE 15

The H-cell apparatus and general procedure of Example 1 are employed.

The catholyte comprises 80 ml. of a 1.27M aqueous titanium(IV) oxysulfate solution which is clear, i.e. without cloudiness or precipitate. The anolyte comprises 40 ml. of 20 (wt/vol) % aqueous sulfuric acid.

A current density of 23.4 to 22 ASD is maintained.

A purple solution forms in the catholyte, no precipitate being observed.

After passing 46.6% of the theoretical current, current efficiency is 82.8%. After passing 88% of the theoretical current, current efficiency is 69.5%.

EXAMPLE 16

The H-cell apparatus and general procedure of Example 1 are followed. The cathode comprises foamed copper.

The catholyte comprises 81 ml. of a clear 1.25M aqueous titanium(IV) oxysulfate solution.

The anolyte comprises 40 ml. of 20 (wt/vol) % aqueous sulfuric acid.

Apparent current density is maintained at 23.4 ASD.

A purple solution forms in the catholyte, no precipitate being observed.

Current efficiency is 93.2% after passing 46.6% of theoretical current, and 81% after passing 88% of theoretical current.

Examples 15 and 16 demonstrate that titanium(IV) oxysulfate can be subjected to higher current densities, i.e. in the range of about 1 to 30 ASD, in a process according to the invention to produce titanium(III) reducing agent at high current efficiencies.

EXAMPLE 17

Titanium(IV) oxysulfate solutions (a)-(e) are prepared by dissolving in water to 100 ml., an amount of titanium(IV) oxysulfate solids (Noah Chemical Corp.) comprising 16.6% free sulfuric acid, 4.9% free water and 19.2% titanium, to give solutions having a titanium concentration and sulfuric acid concentration listed on the following Table.

The solutions when initially prepared have a very slight cloudiness which is removed by filtering through a fine glass sintered filter, without leaving any visible residue on the filter. The resulting solutions are completely clear, i.e. without any cloudiness or precipitate.

| Solution | Titanium (IV) concentration | $H_2SO_4$ concentration |
|---|---|---|
| (a) | 1.0M | 4.15% |
| (b) | 0.5M | 2.0%% |
| (c) | 0.25M | 1.04% |
| (d) | 0.125M | 0.5% |
| (e) | 0.02M | 0.08% |

The solutions are let stand at room temperature. After 240 hours, solutions (a)-(c) remain completely clear, without visible cloudiness or appearance of precipitate. Solution (d) shows a slight cloudiness after 24 hours, which however does not increase for the remaining 216 hours. Solution (e) becomes somewhat cloudy and a white precipitate appears after 48 hours. The results indicate that titanium(IV) oxysulfate solutions remain stable, without hydrolyzing or precipitating solids from solution, at very low acid concentrations, i.e. as low as 1% and possibly lower.

COMPARATIVE EXAMPLE 18

Titanic sulfate, $Ti(SO_4)_2$, is obtained as a clear solution comprising 30% titanic sulfate in 30% sulfuric acid, and is diluted by addition of water to a 6% sulfuric acid solution comprising 6% titanium 0.246M). The resulting diluted solution, when initially prepared, is clear. However, after standing about 10 minutes at room temperature, the titanic sulfate solution develops substantial cloudiness of a milky-white nature, demonstrating the instability of the solution at an acid concentration of 6%.

EXAMPLE 19

A sample of the titanium(IV) oxysulfate solids employed in Example 17 is dissolved in $D_2O$ to a concentration of about 30%, and was subjected to $^{17}O$ Nmr spectroscopy at pulse width, 8 s(about 45° pulse); relaxation delay, 0.2 s; line broadening factor, 12; number of scans averaged, 103,090.

Two sets of signals are observed, comprising: (1) three signals at 733, 743 and 750 ppm (relative to $D_2O$); and (2) a signal at 160 ppm which was assigned to the oxygen atoms of the sulfate group.

The signals in the range of 733-750, are assigned to oxo- and hydroxo- bridges, see Comba et al., Inorg. Chem. 1987, 26 1315-1323, and constitute evidence for the presence of Ti—O—Ti structures in titanium(IV) oxysulfate.

COMPARATIVE EXAMPLE 20

An $^{17}O$ Nmr spectrograph is taken of the titanic sulfate solution employed in Comparative Example 18, following the procedure of Example 19. No signal is detected at 700-800 ppm, providing further evidence that titanic sulfate is a monomeric species which does not contain Ti—O—Ti bridges.

We claim:

1. A process for reducing aromatic nitro compounds to form the corresponding aromatic amine compounds and intermediates therefor which comprises the steps of:

a. electrochemically reducing a titanium(IV)oxy salt in an acidic aqueous electrolyte solution to form a dissolved titanium(III) reducing agent, said titanium(IV)oxy salt being characterized by being hydrolysis stable in a 7% (wt./vol.) strong acid aqueous solution at room temperature over a period of 24 hours, and said titanium(III) reducing agent characterized by being soluble at a concentration of 1 Normal in a 20% (wt./vol.) strong acid aqueous solution at room temperature, and by being reoxidizable to a hydrolysis stable titanium(IV)oxy salt; and b. reacting said titanium(III) reducing agent with an aromatic nitro compound in an aqueous acidic reaction medium for a time sufficient to reduce at least a portion of the amount of the nitro compound to the corresponding amine compound or intermediate therefor and to oxidize at least a portion of the amount of the titanium(III) reducing agent to a soluble, hydrolysis stable titanium(IV-)oxy salt.

2. The process of claim 1 in which the titanium(IV-)oxy salt in step (a) is titanium(IV) oxysulfate.

3. The process of claim 2 which comprises the additional step of recycling the resulting titanium(IV)oxy salt formed in step (b) to step (a).

4. The process of claim 1 wherein in step (a) the aqueous electrolyte solution has a temperature of about 25°-65° C., and the electrochemical reduction is carried out in an electrolytic cell comprising an anode and a cathode, wherein a direct current is applied to the electrodes at a current density of about 1-30 ASD.

5. The process of claim 4 wherein current density is 1-8 ASD.

6. The process of claim 4 wherein the electrolytic cell is an undivided cell in which the anode comprises titanium oxide having the formula $TiO_{[x]}$ where x is 1.55 to 1.95.

7. The process of claim 2 wherein the aqueous electrolyte solution comprises sulfuric acid or an organic sulfonic acid or mixtures thereof and the acid concentration of the solution is about 1 to 50% (wt./vol.).

8. The process of claim 7 wherein acid concentration of the solution is about 5 to 25% (wt./vol.).

9. The process of claim 8 wherein the acid concentration is 10 to 20% (wt./vol.).

10. The process of claim 8 wherein the solution comprises methanesulfonic acid.

11. The process of claim 10 wherein the solution additionally comprises sulfuric acid in a concentration not in excess of 10% (wt./vol.).

12. The process of claim 4 wherein the electrolytic cell comprises a cathodic and an anodic compartment which are separated by a porous barrier, said aqueous electrolyte solution being provided to the cathodic compartment and an anolyte solution being provided to the cathodic compartment.

13. The process of claim 12 wherein the aqueous electrolyte solution comprises sulfuric acid or an organic sulfonic acid or mixture therof and wherein acid concentration is 1-50% (wt./vol.).

14. The process of claim 13 wherein the acid concentration is 1-10% (wt./vol.).

15. The process of claim 13 wherein the acid concentration is 5-20% (wt./vol.).

16. The process of claim 13 wherein the solution comprises a $C_{1-4}$ alkyl sulfonic acid.

17. The process of claim 16 wherein the $C_{1-4}$ alkyl sulfonic acid acid is methanesulfonic acid.

18. The process of claim 17 wherein the solution additionally comprises sulfuric acid.

19. The process of claim 12 wherein the anolyte solution comprises an aqueous (1-50% (wt./vol)) strong acid solution.

20. The process of claim 19 wherein the anolyte comprises a redox agent selected from the group consisting of transition metal salts and hydrogen halides.

21. The process of claim 4 wherein step (b) is carried after the current is removed, and wherein the reaction medium of step (b) comprises the solution formed in step (a).

22. The process of claim 4 wherein the aqueous electrolyte solution comprises the aromatic nitro compound and step (b) is carried out in situ while current is being applied.

23. The process of claim 1 wherein in step (b), the molar ratio of titanium(III) to the aromatic nitro compound is about 6N:1 to 7N:1 wherein N is the number of nitro groups in the aromatic nitro compound.

24. The process of claim 1 wherein in step (b), the acid concentration of the reaction medium is about 1 to 50% (wt./vol.).

25. The process of claim 4 which is conducted in inert atmosphere or by bubbling an inert gas through the aqueous electrolyte solution.

26. The process of claim 1 wherein the aromatic nitro compound is 4,4'-dinitrostilbene-2,2'-disulfonic acid and the aromatic amine compound is 4,4'-diaminostilbene-2,2'-disulfonic acid.

27. The process of claim 26 in which the titanium(IV)oxy salt in step(a) is titanium(IV) oxysulfate.

28. A process for reducing 4,4'-dinitrostilbene-2,2'-disulfonic acid to 4,4'-diaminostilbene-2,2'-disulfonic acid which comprises:
a. electrochemically reducing titanium(IV) oxysulfate in an aqueous strong acid electrolyte solution comprising 1-50 wt./vol. % $C_{1-4}$ alkylsulfonic acid to form a dissolved titanium(III) reducing agent,
said titanium(IV)oxy sulfate being characterized by being hydrolysis stable in a 7% (wt./vol.) sulfuric acid solution at room temperature over a period of 24 hours,
and said titanium(III) reducing agent characterized by being soluble at a concentration of 1 Normal in a 20% (wt./vol.) sulfuric acid solution at room temperature, and by being reoxidizable to a hydrolysis stable titanium(IV)oxy salt; and
b. reacting said titanium(III) reducing agent with 4,4'-dinitrostilbene-2,2'-disulfonic acid in an aqueous acidic reaction medium at a temperature of about 50°-100° C. for a time sufficient to reduce at least a portion of the nitro compound to 4,4'-dinitrostilbene-2,2'-disulfonic acid, thereby reoxidizing at least a part of the titanium(III) reducing agent to form a soluble, hydrolysis stable titanium(IV)oxy salt;
c. separating the amine compound from the resulting solution; and
d. recycling the resulting reoxidized titanium(IV)oxy salt to step (a).

29. The process of claim 28 wherein in step (a) the aqueous electrolyte solution is provided to an undivided electrolytic cell comprising an anode and a cathode, wherein the anode comprises titanium oxide of the formula $TiO_{[x]}$ where x is 1.65-1.9, said solution is maintained at a temperature of about 35°-65° C., and a direct current is applied to the electrodes at a current density of about 1-30 ASD.

* * * * *